United States Patent [19]

Hino et al.

[11] 4,148,689

[45] Apr. 10, 1979

[54] IMMOBILIZATION OF MICROORGANISMS IN A HYDROPHILIC COMPLEX GEL

[75] Inventors: Tsunetoshi Hino, Higashiosaka; Hideaki Yamada; Seizo Okamura, both of Kyoto, all of Japan

[73] Assignee: Sanraku-Ocean Co., Ltd., Tokyo, Japan

[21] Appl. No.: 794,047

[22] Filed: May 5, 1977

[30] Foreign Application Priority Data

May 14, 1976 [JP] Japan .................................. 51-55925
May 27, 1976 [JP] Japan .................................. 51-62041
Feb. 10, 1977 [JP] Japan .................................. 52-13650

[51] Int. Cl.$^2$ ........................ C12K 1/00; C07G 7/02
[52] U.S. Cl. ........................................ 195/65; 195/59; 195/63; 195/68; 195/DIG. 11; 252/449
[58] Field of Search ...................... 195/65, 63, 68, 54, 195/DIG. 11, 59; 260/112 R, 6, 8; 252/449, 451, 452

[56] References Cited

U.S. PATENT DOCUMENTS

3,878,300  4/1975  Milligan .............................. 426/422

FOREIGN PATENT DOCUMENTS

5053583  9/1973  Japan .................................. 195/63

OTHER PUBLICATIONS

Dickey, F., Specific Adsorption, J. Phys. Chem., vol. 59, 1955, pp. 695–707.

Zaborsky, O., Immobilized Enzymes, CRC Press, Cleveland, Ohio, 1973, pp. 89–91.

Kazuo et al., Immobilization of Enzyme by Carrier Containing Organic Polymers and Silanes, Chemical Abstracts, col. 84, 1976 (55915s).

*Primary Examiner*—David M. Naff
*Attorney, Agent, or Firm*—Jacobs & Jacobs

[57] ABSTRACT

Immobilization of microorganisms is carried out by mixing a water soluble-polymer selected from polyvinylalcohol, gelatin and carboxymethylcellulose with a tetraalkoxysilane, hydrolyzing the resulting mixture by the addition of acid to form a homogeneous complex sol, dispersing microbial cells homogeneously in the sol and gelling the mixture of the sol and microbial cells.

14 Claims, 1 Drawing Figure

FIG. 1

IMMOBILIZATION OF MICROORGANISMS IN A HYDROPHILIC COMPLEX GEL

FIELD OF THE INVENTION

The present invention relates to a process for the production of a homogeneous hydrophilic complex by lyogel or xerogel which has desirable compatibility and affinity with a biological substance and is useful as a supporting matrix for microbial cells and as an excellent pharmaceutical material. The invention also comprises a process for immobilization of microbial cells possessing enzymatic activities by entrapping them inside the hydrophilic complex gel matrix under quite mild conditions, which is produced from a water-soluble-polymer and silicate.

Enzymes are biological catalysts possessing extraordinarily high efficiency and specific properties. They may be used to catalyze almost any type of chemical reaction. Enzymatic reactions are accomplished under milder conditions than chemical reactions and do not produce any harmful substances. In recent days serious attention has been focused on the important problem of environmental pollution in the chemical industry.

Accordingly, it is very advantageous to apply enzymes to the chemical industry. Industrial application of enzymes or microorganisms has been accomplished by using intact microorganisms or soluble enzyme preparations. But such biocatalysts can be used just for only a single batch reaction or fermentation. If enzymes and microorganisms can be stabilized and recovered inexpensively without inactivation, it will be possible to use biocatalysts more widely in the industry.

Immobilization of the catalyst offers a means of achieving objectives. Immobilized enzymes are coming into use for technological purposes as well as for medical and analytical purposes. Most immobilization studies concern cell-free enzymes, but in recent years increasing attention has been directed towards the use of immobilized whole microbial cells. These systems obviate the need for cell separation, enzyme extraction and enzyme purification steps prior to immobilization. Immobilized cells are also more applicable to catalyzing sequential reactions and provide a means of regenerating in situ the necessary cofactors. Further, if it should be possible to continuously utilize a multiple enzyme system in the immobilized state, it would mean that the traditional fermentation process could be replaced with one employing immobilized cells.

The disadvantages associated with immobilized cells are the cost of the supporting matrix and the loss of catalytic activity or the difficulty to maintain the integrity of the cells during immobilization. In particular, most microbial cells and enzymes are so unstable that subjecting them to the immobilization process causes a decrease in their enzymatic activities and changes in the specificity of their activities. It is very difficult to develop a practical immobilizing process without the above mentioned disadvantages. Therefore, few easily and widely utilized immobilizing processes have been developed.

The present invention offers a method for immobilization of microbial cells having enzymatic activity under quite mild conditions without decreasing the activity thereof, and describes some desirable chemical, physical and biological properties of the prepared immobilized microbial cells.

PRIOR ART

Method for immobilization of microbial cells are classified into four types: support-binding method, crosslinking method, gel-entrapping method, and microcapsule-entrapping method. Among these types, the gel-entrapping method, by which microbial cells are immobilized in the gel matrix, is widely used in practice. The conventional gel entrapping method, however, have the following defects. By the gel formation processes of entrapping microbial cells, their enzymatic activities are apt to be decreased remarkably because the activities are frequently affected by environmental factors such as temperature, pH, ionic strength, pressure and the like. Therefore, a novel gel formation method which does not have any harmful effect on the stability of enzymes has been desired. Many investigations on crosslinking and gelling have been carried out with various polymer compounds from this point of view. However, physical methods for gelling polymers such as lowering the temperature or adding salts or non-aqueous solvents have not been widely employed since it is generally difficult to obtain permanent gels by these reversible gelling reactions. For example, in Japan Kokai Patent Showa 50-52276, it has been disclosed that enzymes can be entrapped inside the gel matrix of polyvinylalcohol polymers by a method wherein enzymes and polyvinylalcohol polymers are solubilized in water and solidified at preferably $-25°$ C. to $-80°$ C. and melted at room temperature to form the gel entrapping enzymes. But the gel prepared by the abovecited patent disclosure were unstable at comparatively high temperatures such as 60° C. or 70° C., which is the reaction temperature range of glucose isomerase. Furthermore, chemical methods for gel matrix formation by crosslinking reagents are too strong and destructive for utilization with biological substances. This is because of the high reactivity of the crosslinking reagents and the high temperature and the extremely high or low pH of the gelling reaction. For example, when polyacrylamide gel-entrapping method is employed, acrylamide monomer is polymerized with N,N'-methylene-bis-acrylamide in the presence of a catalyst such as ammonium persulfate. In this case, the enzyme is often inactivated by the highly reactive catalyst. Therefore the range of pH and temperature of the gelling reaction must be carefully chosen for the maintenance of the enzymatic activities (S. S. Wang: Biotech & Bioeng, 15, 93, (1973)). And further, the gels obtained must be prohibited from the application in the pharmaceutical and food industries because of the possibility of remaining toxic acrylamide monomer. In Japan Kokai Patent Showa 50-53583, it has been disclosed that enzymes can be entrapped inside the gel matrices of polyvinylalcoholic polymers by method wherein enzymes and polyvinylalcoholic polymers are dissolved in water and mixed with boric acid or sodium borate to form the gel-entrapping enzymes. According to the above-cited patent disclosure, enzymes can be immobilized without remarkable denaturation at gelling temperatures below 45° C. However, as the gels are formed only at alkaline pH, this method can be applied only to alkaline-stable-enzymes. The toxicity of boric acid must also be considered. Other crosslinking methods using such high-energy radiation as γ-ray, electron ray or X-ray are difficult of practical application because they require large equipment and precautions must be taken to prevent the physiological effects associated with high-energy rays (ref. H. Maeda; Biotech. & Bioeng., 15, 607 (1973).

The immobilized enzymes or microorganisms prepared by the conventional gel-entrapping methods are physically weak and are especially low in mechanical strength when in wet condition. So it is difficult to use such gels in continuous reactions over a long period. When the gels are packed in a column for continuous reaction, they are crushed by water pressure and a satisfactory flow rate of the reaction mixture cannot be obtained.

Other prior art in this field is summarized in F. Katchalski & I. Silman, "Effect of the microenvironment on the mode of action of immobilized enzymes": Advance in Enzymology, 34, 445 (1971).

The present inventors have thoroughly studied the formation of homogeneous complex gels from silica and various kinds of organic compounds because silica is a compound which is harmless to bioorganisms and inexpensive as well. When silica sol and silica gel manufactured by conventional methods were mixed with water-soluble-polymer compounds under various conditions no homogeneous complex lyogel containing much water, homogeneous transparent complex lyogel or transparent complex xerogel could be obtained, although the nature of the polymer compounds was considerably changed. For example, when silica sol is added into the aqueous solution of polyvinyl-alcohol (abbreviated as PVA hereinafter), the separation of two layers is observed (5 to 20% silica, 1 to 5% PVA). Above pH 5 the mixture is completely separated into two layers, one containing silica and the other PVA. Under pH 5 the silica disperses into the PVA layer and coacervate is formed. The desired homogeneous transparent sol or gel is not formed at any pH. Furthermore, inorganic silicate salts such as water glass cannot form a homogeneous solution with PVA by acid-hydrolysis, so it is impossible to obtain the desired homogeneous transparent complex gel.

SUMMARY OF THE INVENTION

According to the present invention there is provided a process for preparing a hydrophilic complex gel by mixing a water-soluble-polymer and an organic silicate, particularly, tetraalkoxysilane, and gelling under mild conditions, whereby is obtained a hydrophilic complex gel having no harmful effect on the activity of biological substances such as microbial cells or enzymes and useful for the immobilization of microbial cells possessing enzyme activity and for use as a pharmaceutical material.

It has been found that a tetraalkoxysilane such as tetraethoxysilane is acid-hydrolyzed in an aqueous solution of water-soluble-polymer such as polyvinylalcohol, gelatin, carboxymethylcellulose, starch and sodium alginate, to form a homogeneous complex sol. It has been further found that the formed homogeneous complex sol is gelled to become a water-insoluble xerogel through the drying process. And it has been still further found that microbial cells possessing enzymatic activity can be immobilized by entrapment inside the gel matrix without decrease of the enzymatic activity because the above-mentioned complex sol is gelled under quite mild conditions.

Accordingly, it is the most important object of this invention to provide a hydrophilic gel which is insoluble in water and inexpensive to produce, and has excellent compatibility and affinity with a biological substance.

It is another object of the present invention to provide a hydrophilic gel matrix which is readily applicable to immobilization of microbial cells possessing enzymatic activity.

It is another object of the present invention to provide a novel means for immobilizing microbial cells while maintaining at least more than 50% of th enzymatic activity which was originally shown by the untreated microbial cells.

It is another object of the present invention to provide immobilized microbial cells which can be employed for use in a continuous process with a column reactor or in a batch process with stirring.

Other and further objects will be evident from the following detailed description of the present invention.

DESCRIPTION OF THE PREFERRED EMBODIMENTS

The hydrophilic complex gel according to the present invention is produced by reacting a water-soluble-polymer and a tetraalkoxysilane to form a homogeneous sol and subsequently by gelling under quite mild conditions. The tetraalkoxysilane is acid-hydrolyzed in an aqueous solution of the water-soluble-polymer to form a homogeneous sol. Microbial cells possessing enzyme activity are added to the sol thus obtained. The mixture is gelled by pH adjustment to give a complex lyogel, or dried after the pH adjustment to give a water-insoluble xerogel in which lyogel or xerogel are entrapped without decreasing the enzymatic activity.

The water-soluble-polymer compounds employed in this invention have many polar groups such as —OH group, —COOH group, —NH₂ group, =NH group and so on, which form strong hydrogen bonds with acidic —OH groups of silicate by hydrolysis. The water-soluble-polymer compounds shown in Table 1 below can be used.

TABLE 1

(A) Natural polymer compounds and their derivatives
 1. Celluloses; carboxymethylcellulose, methylcellulose, ethylcellulose, hydroxyethylcellulose.
 2. Starches; hydroxyethylstarch, carboxymethylstarch.
 3. Other polysaccharides; mannan, dextran, chitosan, pullulan, guar gum, locust bean gum, tragacanth, xanthangum, agar, sodium arginate.
 4. Proteins; gelatin, albumin.

(B) Synthetic polymer compounds
 Polyvinylalcohol, polyethyleneglycol, polyethyleneimine.

The preferred water-soluble-polymers employed in the present invention may be a polyvinylalcohol that has an average polymerization degree between 500 and 2,000, and a saponification degree within the range of 70 to 100%; a commercial gelatin of edible grade that has a jelly strength of more than 200 g shot/5 second in Bloom Gelometer; or a carboxymethylcellulose of commercial edible grade that has a carboxylation degree between 0.4 and 0.8 and a sodium content within the range of 7.0 to 8.5%.

The water-soluble-polymer compound is solubilized in water at a concentration having a viscosity below 10,000 centi poise, preferably below 3,000 centipoise for full agitation. The above mentioned viscosity is measured by No. 3 rotor of a B type viscosity meter at 40° C.

The tetraalkoxysilanes which may be used in the present invention are those of the structural formula: $Si(OR)_4$, in which R is alkyl group of up to 12 carbon atoms, e.g., methyl, ethyl, propyl, butyl, octyl and lauryl groups. Compounds in which R represents an alkyl group of up to 3 carbon atoms are preferably utilized for the effective formation of the homogeneous complex sol. Tetraethoxysilane is the most suitable compound.

The water-soluble-polymer compound is mixed with the above-mentioned tetraalkoxysilane, and then the pH of the mixture is adjusted below 3 with acid or acidic salt which exhibits no harmful effect on the enzymatic activities of microbial cells. The acids or the acidic salts which may be used in the present invention are shown in Table 2.

TABLE 2

(A) Inorganic acids: HCl, $HNO_3$, $H_3PO_4$, $H_2SO_4$.
(B) Organic acids: Acetic acid, glutamic acid, lactic acid, maleic acid, succinic acid, ascorbic acid, citric acid, tartalic acid.
(C) Inorganic or organic acidic salt: $AlCl_3$, citrate-1-ammonium.

The amount of tetraalkoxysilane necessary for the above-mentioned mixing with the aqueous solution of water-soluble-polymer varies according to the kind of silane compound and the properties of the water-soluble-polymer employed. The amount of $SiO_2$ contained in the tetraalkoxysilane, calculated based on $SiO_2$ formed by acid-hydrolysis, should be 5 to 300% (w/w) of the dry weight of the water-soluble-polymer. The preferable amount of $SiO_2$ is in the range of between 50% and 200%. When the amount of $SiO_2$ is below 5%, the solubility in water of the formed gel increases significantly, whereas, in case of it being above 300%, the gel becomes fragile. The property of the gel depends on the $SiO_2$ content of the tetraalkoxysilane and/or the chemical structure of the water-soluble-polymer. For example, PVA having an average polymerization degree between 500 and 2,000 and a saponification degree within the range of 70 to 100%, may be used, but the preferred amount of $SiO_2$ is above 20%, more preferably above 50%, in case of completely saponified PVA, while a smaller amount of $SiO_2$ is required for a PVA having a lower saponification degree.

In the initial stage of the reaction process, the mixture of water-soluble-polymer compound and tetraalkoxysilane is separated into two layers because of their mutual insolubilities. After adjusting the pH below 3 by the addition of acid or acidic salt, the mixture is stirred well at room temperature with heating below 80° C., if necessary, to be hydrolyzed completely. The lower the pH and the higher the temperature is, the faster the hydrolytic reaction is, but the conditions are chosen according to the nature of the desired gel. The aqueous solution of PVA and tetraethoxysilane are mixed at such ratio that the $SiO_2$ amount of the tetraethoxysilane is 100% (w/w) of the dry weight of the PVA. The mixture is completely hydrolyzed at pH 3 and room temperature over two hours to form a colorless transparent homogeneous complex sol. The completion of the hydrolysis may be determined by the fact that the boundary of the two separated layers disappears and a homogeneous and transparent solution is obtained. The original specific smell of tetraalkoxysilane changes to an alcoholic perfume.

The formed sol can be preserved for a long period below room temperature. In particularly, no property of the sol is changed at 5° C. even after one month.

As previously mentioned, various kinds of water-soluble-polymer compounds may be used as one of the components of the complex sol. The complex sol can be easily gelled by the pH adjustment or the drying process. The complex gels formed under different conditions from the same water-soluble-polymer compound have various degrees of turbidity. For example, the complex sol of gelatin and tetraethoxysilane is converted to a transparent gel below pH 4. The most turbid gel is obtained at pH 5, and above pH 7, the gel becomes semi-transparent.

The complex gels formed are normally classified into the lyogel type which contains much water inside and the xerogel type which contains little water. In the latter type, the moisture of the gel is almost completely removed through the drying process. According to this invention, the components of the sol are not separated, but maintain the homogeneous complex state throughout the processes of the sol formation→gel formation→xerogel formation. The xerogels prepared are insoluble or hardly soluble in water, but exhibit hydrophilic property.

As shown in the Examples described hereinafter, the properties of the formed xerogel depend on the nature of the water-soluble-polymer employed and also on the ratio of $SiO_2$ to the polymer. Generally the gel becomes more insoluble in water, and harder and more fragile in accordance with the increase of $SiO_2$ amount. In contrast, it becomes more flexible with the increase of the polymer. As for the effect of the water-soluble-polymer (PVA, for example), the properties of the xerogel vary according to the saponification degree of the PVA employed. In the case of completely saponified PVA, the smallest amount of $SiO_2$ required is 50% (w/w) based on the PVA used. But, for the formation of a similar xerogel with partially saponified PVA (87% saponification), the required amount of $SiO_2$ is smaller, but must be at least more than 20% (w/w).

According to the present invention, microbial cells possessing enzymatic activities can be immobilized under quite mild conditions by entrapping them inside the gel matrix of the above-mentioned hydrophilic complex gel produced from the water-soluble-polymer compound and silicate. The microbial cells are added into the above-mentioned homogeneous sol without any pH adjustment or basic salts as shown in Table 3.

TABLE 3

(A) Bases: NaOH, KOH, $Ca(OH)_2$, $NH_4OH$.
(B) Basic salts: $Na_2CO_3$, $CH_3COONa$, $NaHCO_3$, $K_2CO_3$, $K_2HPO_4$, $Na_2HPO_4$, $CH_3COOK$.

The microbial cells which may be used in the present invention are dried cells, wet cells harvested from broth by centrifugation or filtration and the cultured broth itself. These microbial cells are classified into the following 5 groups, bacteria, actinomycetes, fungi, yeast and algae. Bacteria of the first group, belonging to Class Shizomycetes taxonomically, are Genus: Pseudomonas, Acetobacter, Gluconobacter, Bacillus, Corynebacterium, Lactobacillus, Leuconostoc, Streptococcus, Clostridium, Brevibacterium, Arthrobacter, Erwinia and so on. Actinomycetes of the second group, belonging to Class Shizomycetes taxonomically, are Genus: Streptomyces, Nocardia, Mycobacterium and so on. (R. E. Buchran & N. E. Gibbons, "Bergey's mannual of Determinative Bacteriology" 8th edition, (1974); The Williams & Wilkins Company). Fungi of the third group, belonging to Class: Phycomycetes, Ascomycetes, Fungi, imperfecti, and Bacidiomycetes taxonomically, are Genus: Mucor, Rhizopus, Aspergillus, Penicillium, Monascus, Neurosporium and so on (J. A. von ARX, "The genera of Fungi sporulating in pure culture" Verlag von J. Cramer, and H. L. Barnett & Barry B. Hunter, "Illustrated genera of Imperfect Fungi" 3rd edition, (1970); Burgess publishing company). Yeast of the forth group, belonging to Class Ascomycetes, taxonomically, are Genus: Saccharomyces, Zygosaccharomyces, Pichia, Hansenula, Candida, Torulopsis, Rhodotorula, Kloechera and so on (J. Lodder, "The yeast A taxonomic study" 2nd edition (1970); North-Holland publishing company). Algae of the fifth group are single-cell Genus: Chlorella and Scedesmus in green-algae, and single-cell Genus Spirulina in blue-green-algae (H. Tamiya, "Studies on microalgae and Photosynthetic Bacteria" (1963); The University of Tokyo press).

Most of these microbial cells are single-cell-grown organism. The cell sizes of individual microorganisms belonging to the above mentioned groups are different from one another, but the diameter or width of each cell employed in the present invention is within the range of $1-20\mu$. The microbial cells can be dispersed in aqueous solvents. Some kinds of Actinomycetes of the second group and Fungi of the third group are more than $20\mu$ in length. Long sized microbial cells (average length: $50-100\mu$) and/or pellet-shaped microbial cells can be entrapped inside the above mentioned gel matrix, but the amount of entrapped cells is comparatively decreased. Therefore, such microbial cells are preferably shredded to be less than $20\mu$. For this purpose, mechanical homogenization in water may be employed.

Microbial cells used in the present invention, selected from the above mentioned five groups, possess more than one enzymatic activity. The enzymes are classified into the following five groups.

TABLE 4

(A) Oxido-reductases: Glucose oxidase, nitrite reductase, catalase, phenol oxidase, monoamine oxidase, cytochrome c reductase.
(B) Transferases: Glutamate-oxaloacetate-transaminase, 16-membered macrolide 3-acyltransferase, ATP: nucleoside-5' monophosphate pyrophosphotransferase.
(C) Hydrolases: Proteases, glucoamylase, $\alpha$-amylase, isoamylase, lipase, lactase, penicillin amidase, alkaline phosphatase, amino acylase, urease, cellulase.
(D) Isomerases: Glucose isomerase, alanine racemase.
(E) Lyases: $\beta$-Tyrosinase, histidine decarboxylase, tryptophanase.

The enzymes used in the present invention are the intracellular enzymes existing inside the microbial cell or mycelium, or inside the organella of bioorganisms. In the present invention, "activity" means not only enzymatic activity, but also other biological activities, such as for example, activities of inhibitors, co-enzymes, antibiotics, antigens, antibodies and the like.

The pH of the mixture of the complex gel and the microbial cells should be chosen in consideration of the enzyme stability or the properties of the formed gel. Usually, it is adjusted to pH 4–8, preferably 5–7. In the immobilization of microbial cells, the adjustment of pH is not needed in most cases because the microbial cells usually have buffer activity in themselves. The pH of the above mentioned mixture usually falls within 5 to 6.5 after the addition of the cells.

The dry weight of the microbial cells to be added is less than 1,000 (w/w), preferably 20–500% (w/w), based on the dry weight of the homogeneous complex sol. After adding the microbial cells to the homogeneous complex sol, the mixture is stirred well to disperse them homogeneously. The gelling reaction of the sol containing the microbial cells takes place at any temperature. However, as the enzymes are unstable at the higher temperature, the gelling reaction is carried out at a temperature between 0° C. and 70° C., preferably between 10° C. and 40° C. The gelling reaction is usually completed within 10–30 minutes. For example, the sol is fully gelled at pH 6.0 by continuous stirring at room temperature for 10–20 minutes.

One of the most important advantages of the present invention is the mild conditions for the immobilization, under which the enzymatic activities can be maintained throughout the whole processes without remarkable inactivation.

The formed complex gel entrapping microbial cells is dried and converted to the desired shape. The drying process is carried out below 75° C. In the case of yeast cells, the fermentation activity is comparatively stable and the whole process of the present invention may be conducted at room temperature. But, as far unstable bacterial cells such as those used for enzymatic L-tyrosine synthesis, eliminate the whole process is performed below 5° C. in order to maintain the enzymatic activities, and especially, freeze-drying is preferred in the drying process. As long as the temperature is maintained within the above mentioned range, almost no inactivation of the enzyme is observed. For the conversion of the above mentioned lyogel immobilizing microbial cells into various shapes, the conventional methods are employed in the present invention. The molding process can be carried out before or after the drying. Especially, hydrophilic or hydrophobic organic solvents in which the complex lyogel is almost insoluble can be employed for this molding process. The following organic solvents as shown in Table 5 may be used.

TABLE 5

(A) Alcohols: Methylalcohol, ethylalcohol, n-propylalcohol, n-butylalcohol, ethyleneglycol, glycerol.
(B) Ketones: Acetone, methylethylketone.
(C) Ethers: Dioxane, tetrahydrofuran.
(D) Alkanes: n-heptane, n-paraffin.
(E) Aromatics: Benzene, toluene, xylene.
(F) Others: Methylenechloride.

In the present invention, the shapes of the gel-immobilized microbial cells may be the granular-type having a round section and in particularly may be spheres, granules, pellets, filaments and so on. When the molded immobilized microbial cells are packed in a column reactor, they give good results in the continuous reaction. In some cases, the molded immobilized microbial cells may also be the film-type or the strip-type or in the other cases, irregular-granules or powder. The average diameter and/or the thickness of the molded gel containing the microbial cells may be between 0.2 and 5 mm, preferably between 0.4 and 1.0 mm. With the molded gels of this thickness, a desirable contact between the immobilized cells and their substrate can be obtained. Furthermore, a desirable flow rate of the reaction mixture through the column reactor may also be obtained.

The desired shape may be obtained by the method of slit-casting because the complex lyogel entrapping the microbial cells is a soft dough. For example, the lyogel according to the present invention is converted into a long cylinder by slit-casting in an organic solvent or the air, and then dried. And also, the lyogel is formed into round granules by dropping into an organic solvent or air, and subsequently by drying. Thus prepared gels have high specific surface area.

Spray-drying may also be employed for the preparation of the desired shapes. The prepared granules have high specific surface area and good properties for utilization in a column reactor. This method may be advantageously used on an industrial scale from the economical viewpoint.

In the present invention, good results may also be obtained by employing the freeze-drying method. The enzymatic activities of the prepared granules according to the method are satisfactorily maintained even if the method is applied to the heat-unstable microbial cells as shown in Example 16 and 17 described hereafter, where the bacterial cells capable of enzymatic L-tyrosine synthesis were used.

Another preferable shape of the gel is the film-type, which is prepared by spreading the sol over the surface of a plate. This type of the gel may also be advantageously applied to industrial use because it has a high specific surface area and is easily produced. The granules of the immobilized microbial cells may also be obtained by pulverization process. Usually more than 80%, and at least 50%, of the enzymatic activities of the untreated microbial cells can be maintained in the granules prepared by the method.

The above-mentioned immobilized microbial cells prepared according to the present invention are stable and maintain this activities for a long period, at least for a year when stored at 10° C., and can be applied to continuous and batch-repeated reactions. For example, the immobilized microbial cells of glucose isomerase can be used without any loss of the activity in a continuous reaction using a column reactor for 30 days. Throughout the long-period continuous process, pressure drops can be ignored even with comparatively high flow rate and with various degrees of ionic strength.

The immobilized microbial cells according to the present invention can be utilized as the catalysts for biochemical conversion of various substrates not only in the column reactor system, but also in the batch-repeated reactor system. In using the usual batch-repeated reactor system with stirring, no pronounced leaking of the microbial cells from the gel or destruction of the molded gel is observed. Further, the water-soluble-polymer compound can be recovered from the gel immobilizing microbial cells and used repeatedly when the activities have decreased after a long period of use. The water-soluble-polymer compound or the complex sol can be recovered by dissolving the gel in a hot alkaline water, such as aqueous ammonia, removing the cells by centrifugation or filtration, and subsequently adjusting the pH.

The following examples illustrate methods of carrying out the present invention but it is to be understood that they are given for purposes of illustration and not of limitation.

EXAMPLE 1

50 g of 10% PVA (polymerization degree: 2,000 and completely saponified) aqueous solution was mixed with 20 g of water, 5 g of tetraethoxysilane, and 1 g of 1 N HCl and stirred. The turbid mixture gradually became a colorless, transparent homogeneous complex sol at room temperature in two hours. The prepared homogeneous complex sol was neutralized by adjusting the pH to 7.0 with 1 N $NH_4OH$, and a colorless, transparent homogeneous complex lyogel was formed without any separation of the lyogel components such as PVA or tetraethoxysilane. The homogeneous sol was also gelled without neutralization by storing for a long period to form complex lyogel, which also was transparent and homogeneous and insoluble in water of room temperature. The prepared homogeneous complex lyogel was dried by ventilation at room temperature to form a transparent homogeneous complex xerogel, which was insoluble in tap water. The complex xerogel thus obtained was swelled without any separation of the components, when treated in boiling water for an hour. In case of the complex xerogel prepared after neutralizing and drying by ventilation mentioned above, the solubilized amount was 50% of the initial weight of the complex xerogel, and the swelling degree was about 30 fold in boiling water. In case of the complex sol without neutralization, the solubilized amount was 30% and the swelling degree was about 12 fold in boiling water.

EXAMPLE 2

By the same procedure as described in Example 1, except for adding 15 g of tetraethoxysilane, homogeneous complex lyogel was formed. The reaction process, intermediately produced sol and the appearance of resulting lyogel were almost the same as those in Example 1. The complex xerogel formed with or without neutralization was insoluble in tap water. The solubilized amount was less than 3% and the swelling degree was less than 3 fold by treatment in boiling water.

EXAMPLE 3

Employing the same procedure as described in Example 1, except for adding 20 g of tetraethoxysilane instead of 5 g, homogeneous complex lyogel was again formed and was found to have similar appearance (i.e. was colorless and transparent) to that of Example 1. Subsequently formed complex xerogel, with or without neutralization, was harder and more brittle to physical forces than that of Example 1. The gel was insoluble in tap water, the solubilized amount being about 2% and the swelling degree about 2 fold in boiling water.

EXAMPLE 4

By the same procedures as described in Example 1, except for adding 2 g of tetraethoxysilane into 5 g of 10% PVA (polymerization degree: 1,700 and saponification degree: 87) aqueous solution, the homogeneous complex lyogel was formed and was found to have very similar appearance to that of Example 1. The complex xerogel formed with or without neutralization was insoluble in tap water and the solubilized amount was less than 9% and the swelling degree was less than 6 fold in boiling water.

EXAMPLE 5

A similar reaction was proceeded as in Example 4, using 10 g of tetraethoxysilane and 5 g of 10% PVA (polymerization degree: 1,700 and saponification degree: 87) aqueous solution. The reaction characteristics and the appearance of the complex sol and resulting homogeneous complex lyogel were almost the same as that of Example 1. The final complex xerogel obtained with or without neutralization was insoluble in tap water and its solubilized amount was about 4% and the swelling rate about 2.5 fold in boiling water.

EXAMPLE 6

2 g of tetraethoxysilane was added with stirring at room temperature to a mixture of 20 g of 5% PVA (polymerization degree 1100, completely saponified) aqueous solution and 0.5 g of aluminum chloride. Stirring was continued for about 2 hours and a colorless, transparent and homogeneous complex sol was obtained. The sol thus formed was dried under ventilation to give a film of transparent homogeneous complex xerogel. This film was insoluble even by extraction in boiling water and maintained its original film shape. The above mentioned sol was also neutralized with 1 N $NH_4OH$ causing the sol to turn white-turbid. It was then dried in ventilation to give a semi-transparent xerogel. The final gel was insoluble in tap water and maintained its original shape in boiling water.

EXAMPLE 7

100 g of 5% gelatin aqueous solution was diluted into 66 g of water, stirred well with heating, and added with 15 g of tetraethoxysilane. After adjusting the pH to 3 or below with diluted HCl, the mixture was stirred continuously at room temperature for 3 hours after which the mixture turned transparent. The homogeneous complex sol so formed was left to stand at room temperature to obtain a transparent homogeneous complex lyogel. After the pH of the lyogel was adjusted with diluted $NH_4OH$, the complex gel became turbid at about pH 4.5 and very turbid at about pH 5 to 6, but again returned to be semi-transparent at above pH 7. Homogeneity was maintained and no water layer was not observed. The pH value influenced the standing period for formation of the complex lyogel. By drying homogeneous complex sols and homogeneous complex lyogels, there were obtained homogeneous complex xerogels having various degrees of turbidity according to the pH variation (transparent in acidic range, whitely turbid at about pH 5 to 6, and semi-transparent above pH 8). The xerogel was insoluble in water at room temperature and swelled in boiling water without loosing its original shape.

EXAMPLE 8

100 g of 5% soluble starch aqueous solution was diluted into 66 g of $H_2O$, and after stirring homogeneously with heating, 15 g of tetraethoxysilane was added. After adjusting the pH to 3 with diluted $H_3PO_4$ solution, the mixture was stirred at room temperature for about 2 hours until a transparent homogeneous complex sol was formed. This sol was neutralized with diluted NaOH and after about 30 minutes storage homogeneous complex lyogel was obtained. Either drying under ventilation of the homogeneous complex sol without neutralization, or drying under ventilation of the homogeneous complex lyogel formed after neutralization, led to formation of whitely turbid xerogel which was brittle to physical force. Only a small amount of starch was extracted from the xerogel in tap water and 50% was extracted in boiling water. The original shape was preserved in both cases and swelling occurred particularly in boiling water.

EXAMPLE 9

100 g of 5% carboxymethylcellulose aqueous solution was added into 66 g of water the the mixture was stirred well at 45° C., and then 20 g of tetraethoxysilane was added to the mixture. The pH of the mixture was adjusted to 3 with 1 N HCl. The mixture was continuously stirred for about two hours until a transparent homogeneous complex sol was radially formed. Further, by adjusting the pH of sol to 6.0 with 1 N $NH_4OH$ and drying under ventilation, a transparent homogeneous complex xerogel was obtained. The homogeneous complex xerogel was insoluble and did not swell in water at room temperature. Even in boiling water, it was almost insoluble and the swelling degree was about 2 fold.

EXAMPLE 10

15 g of tetraethoxysilane was added to 100 g of 5% aqueous polyacrylate solution diluted with 66 g water and the mixture was stirred at room temperature for about 2 hours. The mixture gradually became a transparent homogeneous complex sol, which was neutralized with 17 g of 1 N $NH_4OH$ and stored for the formation of semi-transparent complex lyogel. The homogeneous complex sol formed without neutralization and the homogeneous complex lyogel formed by neutralization were dried to give respective white semi-transparent xerogels. About a half part of the xerogel thus obtained was dissolved in boiling water and the other half remained as the soft hydrogel insoluble in boiling water.

EXAMPLE 11

15 g of tetraethoxysilane was added to 100 g of 5% polyethyleneglycol (#4,000) aqueous solution diluted with 66 g of water and the mixture was stirred at room temperature. By addition of 1 g of 1 N HCl, over 3 hours, the mixture became a colorless and transparent homogeneous sol. This sol was neutralized with 1 N $NH_4OH$ and stored for 3 hours to form a colorless transparent and homogeneous complex lyogel. By drying the lyogel, a colorless transparent and homogeneous complex xerogel was obtained. In boiling water, 50% of the formed xerogel was dissolved to leave a turbid gel. This solid xerogel was rather susceptible to destruction.

EXAMPLE 12

100 Parts of 10% PVA aqueous solution (polymerization degree: 1,700 and saponification degree: 99.5) were mixed with 231.5 parts of distilled water, 28.5 parts of tetraethoxysilane and 1 part of 1 N HCl, and stirred for more than two hours at room temperature to give a transparently homogenized sol at about pH 3, containing 5% of solid part (abbreviated as PVA-$SiO_2$ complex sol hereinafter). One part of commercially available dried baker's yeast (*Saccharomyces cerevisiae*) was suspended into 2 parts of water and was then mixed with PVA-$SiO_2$ complex sol. After the yeast was dispersed homogeneously by stirring, the pH was adjusted to 7.0 with 1 N NH$_4$OH solution. The gel was poured into a petri dish and dried spontaneously at room temperature. A yellowish brown film containing the yeast cells was obtained. A strip of the film immobilizing 1 g of the yeast cells was taken out and incubated in 50 g of 5% glucose aqueous solution at 30° C. to carry out the fermentation test. A large amount of gas production began in a few minutes and in thirty minutes a large amount of gas production was observed from the whole surface of the film. The film swelled a little and decolorized, but the shape showed no change, and the bubbling continued for 30 hours. The reaction was estimated by the measurement of the weight decrease of the medium by liberation of CO$_2$ gas. The reaction was carried out in proportion to the reaction time. A slight fragrant smell peculiar to alcoholic fermentation was detected. Increase in the turbidity of glucose solution, which is considered to come from the leaking yeast cells from the film, was hardly observed, and hence, the mixture was almost transparent. As a control, the same reaction was conducted by using 1 g of dried yeast cells not immobilized. At the very initial stage of reaction, a slightly large amount of CO$_2$ was generated by using the control cells than the immobilized cells but, after 30 hours incubation, the rate of CO$_2$ gas liberation from both media became almost equal. Accordingly, this fact indicated that the unit activity in both cases, native and immobilized cells, was almost comparable to each other, and hence, inactivation of enzymes in the immobilized cells did not occur during the immobilizing process of yeast cells. As a matter of course, since the non-immobilized cells were suspended in the medium, mild agitation was required for securing the progress of reaction. From the above results, it was demonstrated that the microbial cells were firmly immobilized by the present process while maintaining fermentation activity equal to that of the native cells.

EXAMPLE 13

The same PVA-SiO$_2$ complex sol as described in Example 12 was used. 4 parts of commercially available dried yeast (Saccharomyces cerevisiae) was suspended in 5 parts of water. The suspension was mixed in 20 parts of the PVA-SiO$_2$ complex sol and the gel was spread on a plate and dried by ventilation to obtain a yellowish brown film containing yeast cells. A strip of the film containing 1 g of immobilized cells was shred, and incubated in 50 g of 5% glucose aqueous solution at 30° C. to carry out fermentation as in Example 12. A large amount of CO$_2$ gas was liberated even in the early stage of incubation as observed in the control experiment. After terminating the fermentation, the film was taken out of the medium and soaked in another 50 g of 5% glucose aqueous solution again, liberation of CO$_2$ gas was again observed as much as in the previous test with native cells. This fermentation test was repeated 5 times, and the film in glucose solution showed almost the same fermentation activity every time. The same fermentation test using 1 g of non-immobilized cells was carried out to compare the results with that for the immobilized cells. In these tests, the yeast cells were collected by centrifugation and resuspended into the medium. In each test, the amount of CO$_2$ gas liberated from 50 g of 5% glucose aqueous solution was more than 85% of the theoretical value.

EXAMPLE 14

100 Parts of 10% PVA aqueous solution (polymerization degree: 2,000, and saponification degree: 88) were mixed with 181 parts of water, 18 parts of tetraethoxysilane and 1 part of 1 N HCl, and then, the mixture was stirred well for more than two hours at room temperature to obtain a homogeneous and transparent sol at about pH 3, containing 5% of solid part. 2 parts of commercially available dried baker's yeast (Saccharomyces cerevisiae) were suspended in 4 parts of water. The suspension was mixed with 20 parts of the PVA-SiO$_2$ complex sol and thoroughly stirred. The gel, thus obtained, was spread on a plate and dried by ventilation at room temperature to obtain a yellowish brown film containing 1 g of yeast cells. This film containing 1 g of of yeast cells was used for the fermentation test in the same procedures as in Example 12. The fermentation proceeded at an intermediate rate between those of Example 12 and Example 13. That is, the amount of CO$_2$ gas liberation at the initial reaction stage was slightly smaller than that of non-immobilized cells, but the amount of CO$_2$ gas liberated up to the final stage of reaction reached to 85% of the theoretical value. This is almost comparable to the result for non-immobilized cells.

EXAMPLE 15

100 Parts of commercial gelatin for food uses were mixed with 15 parts of tetraethoxylsilane, 66 parts of water and 5 parts of 1 N HCl, and stirred well for more than two hours at around 50° C. to give a transparent and homogeneous complex sol of about pH 3, containing 5% of solid parts. 2 Parts of commercially available dried baker's yeast was suspended in 3 parts of water and this suspension was added to 20 parts of PVA-SiO$_2$ complex sol and stirred to be homogeneous. The gel was spread on a plate and a yellowish brown film containing immobilized yeast cells was obtained by drying at room temperature. The film thus obtained was more fragile and friable than the film made of PVA-SiO$_2$ complex in Examples 12, 13 and 14. A strip of the above mentioned film containing 1 g of immobilized cells was shred, soaked in 50 g of 5% of glucose aqueous solution, and the fermentation test was carried out in a similar way to Example 14. CO$_2$ gas generated throughout the fermentation test amounted to more than 85% of theoretical value. During the fermentation test, no microbial cells were observed to leak out through the film. This fact demonstrated that the yeast cells were firmly immobilized by the present process.

EXAMPLE 16

PVA-SiO$_2$ complex sol was prepared by the same procedures as in Example 12, and Erwinia herbicola (ATCC 21434), a strain producing β-tyrosinase, was cultivated in the following culture medium.

| L-Tyrosine | 0.2 | g/100 ml |
|---|---|---|
| KH$_2$PO$_4$ | 0.05 | g/100 ml |
| MgSO$_4$ | 0.05 | g/100 ml |
| Pyridoxine HCl | 0.01 | g/100 ml |
| Glycerin | 0.6 | g/100 ml |
| Fumaric acid | 0.7 | g/100 ml |
| L-Phenylalanine | 0.2 | g/100 ml |
| DL-alanine | 0.4 | g/100 ml |
| Glycine | 0.3 | g/100 ml |
| Monosodium glutamate | 0.45 | g/100 ml |
| Aji-eki | 1.0 | g/100 ml |

| | |
|---|---|
| $Zn^{++}$ | 2.0 ppm |
| $Fe^{++}$ | 2.0 ppm |
| Final pH | 7.5 |

4 g of cultivated cells (dry weight: 1 g) of the β-tyrosinase producing bacterium was collected by centrifugation and immobilized by the same manner described in Example 12 except the freeze-drying was employed. All the processes of this preparation were carried out below 5° C. The enzymatic activity of β-tyrosinase of the above mentioned immobilized cells containing 20 mg of bacterial cells was determined by measuring the synthesized L-tyrosine in the following L-tyrosine synthesized medium.

| Composition of the medium for L-tyrosine formation: | |
|---|---|
| Sodium pyruvate | 3.0 g |
| Ammonium acetate | 5.0 g |
| EDTA | 0.3 g |
| Sodium sulfite | 0.2 g |
| Pyridoxal phosphate | 0.01 g |
| Phenol | 0.1 g |
| Water | residue |
| Final volume | 100 ml |
| Final pH | 8.0 |

As shown in Table 6, the relative activities for L-tyrosine synthesis of immobilized bacterial cells prepared in Example 16 were about 85% or more than 85% of the activity of the control using nonimmobilized bacterial cells. The activities of the immobilized bacterial cells were proved to be excellent. Further, one gram of the immobilized bacterial cells obtained in Experiment 3 in Table 6 was packed in a column into which the reaction mixture of L-tyrosine synthesis was added continuously at a flow rate of 5 ml/hour to synthesize L-tyrosine. A steady state of L-tyrosine synthesis in the column was achieved after 12 hours of continuous medium supply. This state was maintained even after 24 hours of the start of medium supply and the rate of reaction was kept at about 0.6 mg/ml.

Table 6

| | Bacterial Wet Cells (g) | $H_2O$ (g) | PVA-$SiO_2$ complex Sol (g) | 1N $NH_4OH$ (g) | Dried cells/ Total solid | Relative activity (%) |
|---|---|---|---|---|---|---|
| Control - | 4 | — | — | — | | 100 |
| Exp. 1 | 4 | 7 | 40 | 0.4 | 1/3 | 90.4 |
| Exp. 2 | 4 | 7 | 20 | 0.2 | 1/2 | 89.0 |
| Exp. 3 | 4 | 7 | 10 | 0.1 | 2/3 | 85.6 |
| Exp. 4 | 4 | 7 | 6.7 | 0.067 | 3/4 | 84.2 |
| Exp. 5 | 4 | 7 | 4.0 | 0.04 | 5/6 | 88.3 |

EXAMPLE 17

PVA-$SiO_2$ complex sol was prepared with the same composition as in Example 1. In the same manner as Example 16, 4 g of bacterial cells (1 g on dry weight basis) of beta-tyrosinase activity was suspended to 6 g of water. And then the suspension was mixed with 20 g of the PVA-$SiO_2$ complex sol chilled below 5° C. and homogenized. After the pH of the gel was adjusted to 7.0 with 1 N $NH_4OH$, the gel was extruded into acetone, methylenechloride and iso-propylalcohol, respectively, which were cooled in dried ice-acetone bath. The extruded gels were freeze-dried immediately to give a granular form of immobilized bacterial cells preparation. The formation of L-tyrosine was tested by using 40 mg of each said granular immobilized preparation.

As shown in Table 7, the relative rate of L-tyrosine formation of each preparation was more than 50% of that of 40 mg of non-immobilized bacterial cells which were employed as control (100%). The preparation made by using methylene chloride had more than 70% of relative activity. During the formation of L-tyrosine, no bacterial cell leaked out from the immobilized bacterial cell preparation of granular form.

Table 7

| | Bacterial wet cells (g) | $H_2O$ (g) | PVA-$SiO_2$ complex sol (g) | Organic solvent | Dried cells/ Total solid | Relative activity (%) |
|---|---|---|---|---|---|---|
| Exp. 6 | 4 | 6 | 20 | Acetone | ½ | 54.0 |
| Exp. 7 | 4 | 6 | 20 | Methylene chloride | ½ | 70.5 |
| Exp. 8 | 4 | 6 | 20 | Iso-propyl-alcohol | ½ | 61.1 |

EXAMPLE 18

100 parts (weight parts: the same hereinafter) of 10% PVA aqueous solution (polymerization degree: 1,700; and saponification degree: 99.5) were mixed with 231.5 parts of distilled water, 28.5 parts of tetraethoxysilane and 1 part of 1 N HCl, and stirred for more than 2 hours at room temperature, to form a transparent homogenized sol (abbreviated as complex sol) contain 5% of solid parts having a pH of around 3. 5 parts of commercially available microbial cells of glucose isomerase (Nagase Sangyo Co., Ltd.; commercial name: GI-1150, taxonomical name: *Streptomyces albus*) were suspended in 10 parts of water after shredding the mycelium with a homogenizer at 18,000 rpm for 3 minutes. And then, the prepared suspension was added into 20 parts of the complex sol and dispersed by stirring after the adjustment of pH to 6.0 with 1 N HCl to form a gel. The gel was poured in a petri dish and dried under ventilation at 55° C. and the brown film immobilizing cells was obtained. The film was ground in mortar, and sieved through a 16 mesh sieve to obtain fine granule. The immobilized microbial cells of glucose isomerase thus prepared showed a specific activity of 925 units per gram and the activity of the glucose isomerase was 88% of that of the original cells.

A unit of the enzyme was defined as the amount of the enzyme that produced 1 mg of D-fructose under the following assay conditions: the reaction mixture contained 0.1 M D-glucose and 0.005 M $MgSO_4.7H_2O$, and the reaction was carried out at pH 7.2 at 70° C. for 1 hour.

Figure 1:
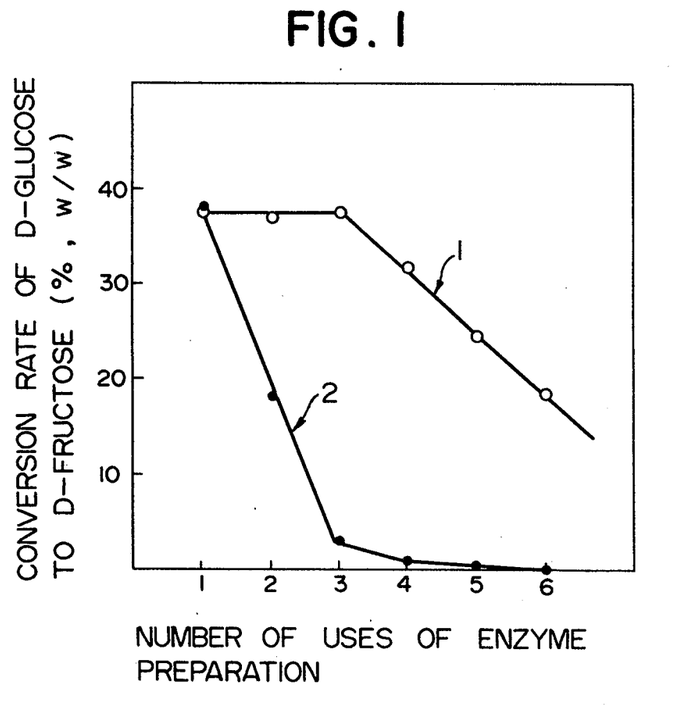
FIG. 1 gives the relation between the conversion rate of D-glucose to D-fructose and the number of uses of the enzyme preparation. The ordinate axis represents the conversion rate expressed in "% in weight" and the abscissa axis represents the number of uses expressed by "times". Curves 1 and 2 show the results obtained with immobilized cells and untreated cells, respectively.

Granular immobilized cells containing 1 g of dried cells were incubated with 100 ml of 40% D-glucose solution containing 0.005 M $MgSO_4$ at 70° C. for 24 hours. After the incubation, the immobilized cells were separated by filtration and repeatedly used for the same reaction 6 times to examine the stability of the enzyme activity in the prepared immobilized cells. 1 g of the native cells on dry weight basis was incubated under the same conditions. The results are shown in FIG. 1. In FIG. 1, the ordinate of the graph represent the percentages of D-fructose to the total solid content of the reaction mixture after each reaction, and the abscissa represents the number of uses in the reaction. It was found from FIG. 1 that the amount of fructose formed was reduced to about half of that in the initial reaction after 6 reuses in case of immobilized cells and was reduced to about half only after 2 reuses in case of non-immobilized cells.

EXAMPLE 19

50 g of the immobilized cells of glucose isomerase prepared by the same procedures as described in Example 18 was packed in a 2.5×20 cm column maintained at 65° C. (the volume of the immobilized cells was 80 ml), and used for the continuous isomerization reaction of 60% D-glucose solution containing 0.005 M $MgSO_4$ at pH 7.5, at the flow rate of SV 1, and the reacted solution was collected. The percentage of D-fructose amounts to the solid content of the reacted solution were maintained at around 50% for 30 days, and gradually decreased to less than 25% after 38 days.

SV 1 was defined as the flow rate that the same volume of the reaction mixture as the apparent volume of the immobilized cells packed in the column, flows in an hour.

EXAMPLE 20

The immobilized microbial cells of glucose isomerase activity prepared by the same procedures described in Example 18 were packed in a column reactor and the pressure drops by flowing water according to the method of T. Fukushima et al. ("Immobilized Enzyme Technology", p. 225 (1975) edited by H. Weethall and S. Suzuki, Plenum press, New York—London) were measured. The average diameter of the immobilized microbial cells of glucose isomerase activity was 0.099 cm. The diameter of the column reactor D, was 1.24 cm, and the length of the reaction bed, L, was 6.4 cm. Water was passed at the rate of V=58 cm/hour by up-flow method. It was found that the pressure drop $\Delta P/L$ was 0.315 $mH_2O/mBed$. The polyacrylamide gel immobilized microbial cells having glucose isomerase used as a control showed pressure drop $\Delta P/L$=5.438 $mH_2O/mBed$, under the same conditions.

EXAMPLE 21

The complex sol was prepared by the same procedures described in Example 18. The filamentous fungi producing glucose oxidase (*Asperigillus niger* IAM2020) was cultured in shaker flasks containing the following culture medium at 30° C. for 3 days.

| Composition of the culture medium for glucose oxidase production: | |
|---|---|
| Soluble starch | 3.0 % |
| Peptone | 0.5 % |
| Meat extract | 0.3 % |
| $KH_2PO_4$ | 0.01% |
| $MgSO_4$ | 0.01% |
| $FeSO_4$ | 0.001% |
| Final pH | 6.0 |

The broth was harvested by filtration. 4 g of the wet cells (calculated 1 g on dry weight basis) was suspended in 10 ml of 0.1 M phosphate buffer saline, pH 7.0 and the mycelium were shred by a homogenizer at 18,000 rpm for 3 minutes. The prepared suspension was added into 10 g of $PVA-SiO_2$ complex sol and stirred at room temperature for 15 minutes. The mixture was poured into a petri dish and ventilated at room temperature to obtain 1.5 g of the yellowish brown film of immobilized cells. 1 g of non-immobilized wet cells had 240 units of glucose oxidase activity while 1 g of the prepared immobilized cells had 510 units of the activity. The recovery of glucose oxidase activity through this immobilization process was 87% per gram of cells.

A unit of glucose oxidase activity was defined as the amount of enzyme that oxidized 1$\mu$ mole of glucose in one minute.

EXAMPLE 22

100 Parts of 5% commercial edible-gelatin aqueous solution heated at 50° C. to be agitatable, were mixed with 15 parts of tetraethoxysilane, 66 parts of water and 5 parts of 1 N HCl, and stirred for more than 2 hours to form a transparent homogeneous complex sol. The prepared sol had 5% solid content and showed about pH 3. On the other hand, *Chlorella fusca* producing nitrite reductase in the cells was cultivated in the following medium with aeration at 25° C. for 4 days.

| Composition of the culture medium for nitrite reductase production: | |
|---|---|
| Glycerin | 0.3 % |
| Na nitrite | 0.25 |
| $KH_2PO_4$ | 0.13 |
| $MgSO_4$ | 0.24 |
| KCl | 0.16 |
| $FeSO_4$ | 0.0002 |
| Final pH | 6.8 |

The cultured cells were harvested by filtration, and 6 g of wet cells (calculated 1 g on dry weight basis) was suspended in 10 ml of water. The prepared suspension was mixed with 10 ml of gelatin-$SiO_2$ complex sol and stirred at room temperature for 15 minutes. The prepared mixture was poured into a petri dish and freeze-dried to obtain 2.1 g of dark green film containing the immobilized cells. 1 g of non-immobilized wet cells had 2.6 units of nitrite reductase activity, and 1 g of the immobilized cell preparation had 6.2 units of activity. The recovery of nitrite reductase activity through this immobilization process was 83% per gram of cells.

A unit of nitrite reductase activity was defined as the amount of the enzyme that reduced 1$\mu$ mole of nitrite at 30° C. for one minute.

EXAMPLE 23

100 Parts of 10% PVA aqueous solution (polymerization degree: 1,700; saponification degree; 99.5) was mixed with 221 parts of distilled water, 36 parts of tetrapropoxysilane, and 3 parts of 1 N HCl, and stirred well with heating at 50° C. for more than about 2 hours to form transparent homogeneous complex sol. The prepared sol had about 5% solid content.

One part of commercial dried baker's yeast (Oriental Yeast Co., Ltd.) was suspended in 2 parts of water and the suspension was mixed with the above prepared sol and dispersed well by stirring. The pH was adjusted to about 6 with 1 N $NH_4OH$. The mixture was poured into a petri dish and ventilated spontaneously below 30° C. to obtain a yellowish brown film of immobilized cells. A fermentation test was carried out in 50 g of 5% glucose aqueous solution at 30° C. employing a part of the prepared film containing 1 g of the dried cells. The fermentation progressed well and the generation of $CO_2$ was observed. The amount of the generated $CO_2$ gas was about 80% of the theoretical value. And further, the leaking of cells could not be observed during the reaction, so no turbidity of the reaction mixture was observed throughout the fermentation test.

EXAMPLE 24

100 Parts of 10% PVA aqueous solution (polymerization degree: 1,700; saponification degree: 99.5) was mixed with 27 parts of distilled water, 27 parts of tetramethoxysilane and 2 parts of 1 N HCl, and stirred well at room temperature for more than 2 hours to form a homogeneous transparent sol. The prepared sol had 5% solid content. 2 parts of commercial microbial cells of glucose isomerase activity (Nagase Sangyo Co., Ltd., commercial name: GI-1150, taxonomical name: *Streptomyces albus*) were immobilized in 20 parts of this complex sol by the same procedure described in Example 18. The recovery of the activity through this immobilizing process was 82%.

EXAMPLE 25

100 Parts of 5% commercial edible-gelatin aqueous solution was heated to 50° C. to be agitatable and was mixed with 13 parts of tetramethoxysilane, 85 parts of distilled water, and 5 parts of 1 N HCl and stirred for more than 2 hours, to prepare a transparent homogeneous complex sol. The prepared sol had about 5% solid content. 2 parts of commercial dried baker's yeast was suspended into 3 parts of water and mixed into 20 parts of this complex sol with stirring to form a homogeneous solution. The mixture was poured into a petri dish and ventilated to obtain a yellowish film of immobilized cells. The prepared film was brittle and easily destroyed. A fermentation test was carried out using a strip of the prepared film containing 1 g of dried cells. The amount of generated $CO_2$ was more than 80% of the theoretical value. And further, the leaking of cells was not observed, indicating perfect immobilization.

EXAMPLE 26

100 Parts of 5% carboxymethylcellulose (commercial food additive) was mixed with 27 parts of tetraethoxysilane, 118 parts of distilled water and 5 parts of 1 N HCl, and stirred at room temperature for more than 2 hours to prepare a complex sol. The sol was homogeneous, but rather more turbid than the sol of PVA. 3 parts of commercial dried yeast (Oriental Yeast Co., Ltd.) was immobilized with 20 parts of the complex sol with the same procedure described in Example 23. The film of immobilized cells was rather brittle and easily destroyed in dried condition. A fermentation test was carried out using a strip of the prepared film containing 1 g of the dried cells in the same manner as described in Example 23. The amount of generated $CO_2$ was more than 85% of the theoretical value, and further, no leaking of cells from the immobilized bed was observed.

EXAMPLE 27

100 Parts of 5% carboxymethylcellulose aqueous solution (a commercial food additive) was mixed eliminate with 195 parts of tetramethoxysilane, 125.5 parts of distilled water and 5 parts of 1 N HCl to prepare a complex sol by the same procedure described in Example 23. The properties of the film immobilized cells were almost the same as those of Example 25. The amount of generated $CO_2$ in the fermentation test was more than 80% of the theoretical value, and as in Example 23 no leaking of cells was observed.

We claim:

1. A process for producing a hydrophilic complex xerogel in which microbial cells are immobilized, which comprises mixing an aqueous solution of a water-soluble-polymer compound selected from the group consisting of polyvinylalcohol, gelatin and carboxymethylcellulose with a tetraalkoxysilane of the general formula: $Si(OR)_4$, wherein R represents an alkyl group of up to 12 carbon atoms, hydrolyzing the resulting mixture by addition of an acid or acidic compound to form a transparent homogeneous complex sol, and dispersing the microbial cells in said sol homogeneously, at a pH between 4 and 8 and subsequently gelling the mixture of said sol and said microbial cells by drying, the amount of said tetraalkoxysilane, calculated based on $SiO_2$ formed by acid hydrolysis, being 5 to 300% by weight of the dry weight of said water-soluble-polymer.

2. The process according to claim 1, wherein R of said tetraalkoxysilane is an alkyl group of up to 3 carbon atoms.

3. The process according to claim 1, wherein said water-soluble-polymer compound is polyvinyl-alcohol and said tetraalkoxysilane is tetraethoxysilane.

4. The process according to claim 1, wherein the weight of $SiO_2$ contained in said tetraalkoxysilane is at least 20% of the dry weight of said water-soluble-polymer compound.

5. The process according to claim 1, wherein the size of said microbial cell is within about 0.5 to 1.5$\mu$ in width, and within about 1 to 20$\mu$ in length.

6. The process according to claim 1, wherein the mixture of said homogeneous complex sol and said microbial cells is dried at a temperature between 0° and 70° C.

7. The process according to claim 1, wherein the dry weight of said microbial cells is 20 to 1,000% of that of said homogeneous complex sol.

8. A process for producing a hydrophilic complex xerogel in which microbial cells are immobilized which comprises mixing an aqueous solution of a water-soluble-polymer compound selected from the group consisting of polyvinylalcohol, gelatin and carboxymethylcellulose with a tetraalkoxysilane of the general formula: $Si(OR)_4$, wherein R represents an alkyl group of up to 12 carbon atoms, and hydrolyzing the resulting mixture by addition of an acid or acidic compound to form a transparent homogeneous complex sol, and dispersing the microbial cells in said sol homogeneously at a pH between 4 and 8, and gelling the mixture of said sol and said microbial cells by casting into organic solvent and drying, the amount of said tetraalkoxysilane, calculated based on $SiO_2$ formed by acid hydrolysis, being 5 to 300% by weight of the dry weight of said water-soluble-polymer.

9. The process according to claim 8, wherein R of said tetraalkoxysilane is an alkyl group of up to 3 carbon atoms.

10. The process according to claim 8, wherein said water-soluble-polymer compound is polyvinyl-alcohol and said tetraalkoxysilane is tetraethoxysilane.

11. The process according to claim 8, wherein the weight of $SiO_2$ contained in said tetraalkoxysilane is at least 20% of the dry weight of said water-soluble-polymer compound.

12. The process according to claim 8, wherein the size of microbial cell is within about 0.5 to 1.5$\mu$ in width, and within about 1 to 20$\mu$ in length.

13. The process according to claim 8, wherein the mixture of said homogeneous complex sol and said microbial cells is dried at a temperature between 0° C. and 70° C.

14. The process according to claim 8, wherein the dry weight of said microbial cells is 20 to 1,000% of that of said homogeneous complex sol.

* * * * *